United States Patent [19]
Hearne

[11] 4,420,001
[45] Dec. 13, 1983

[54] RESPIRATORY MEASURING DEVICES

[76] Inventor: Keith M. T. Hearne, Flat C, 17, Pearson Ave., Hull. North Humberside, England, HU5 2SX

[21] Appl. No.: 112,983

[22] Filed: Jan. 17, 1980

[30] Foreign Application Priority Data

Jan. 19, 1979 [GB] United Kingdom ............... 7902117

[51] Int. Cl.³ ............................................. A61B 5/08
[52] U.S. Cl. ............................... 128/724; 128/419 R
[58] Field of Search ................. 128/724, 716, 419 R, 128/1 C

[56] References Cited

U.S. PATENT DOCUMENTS

| | | | |
|---|---|---|---|
| 2,831,181 | 4/1958 | Wamer | 128/724 |
| 3,232,288 | 2/1966 | Krobeth | 128/724 |
| 3,316,902 | 5/1967 | Winchel et al. | 128/724 X |
| 3,802,417 | 4/1974 | Lang | 128/724 X |
| 3,999,537 | 12/1976 | Noiles | 128/724 |

*Primary Examiner*—Lee S. Cohen
*Attorney, Agent, or Firm*—William A. Drucker

[57] ABSTRACT

The invention relates to a respiration measuring device comprising, in combination, a temperature sensitive element intended to locate in a breathing duct, or the air flows to and from a breathing duct, a control for counting temperature changes sensed by said temperature sensitive element, and an alarm actuated by said control when the rate of temperature changes sensed by said temperature sensitive element rises above, or falls below, a predetermined value. The device may be used by a second party to monitor the breathing rate of the person to whom the device is attached but the device has particular use when self administered, for arousing a sleeper from an unpleasant dream state to a wakeful or a lucid dream state.

7 Claims, 1 Drawing Figure

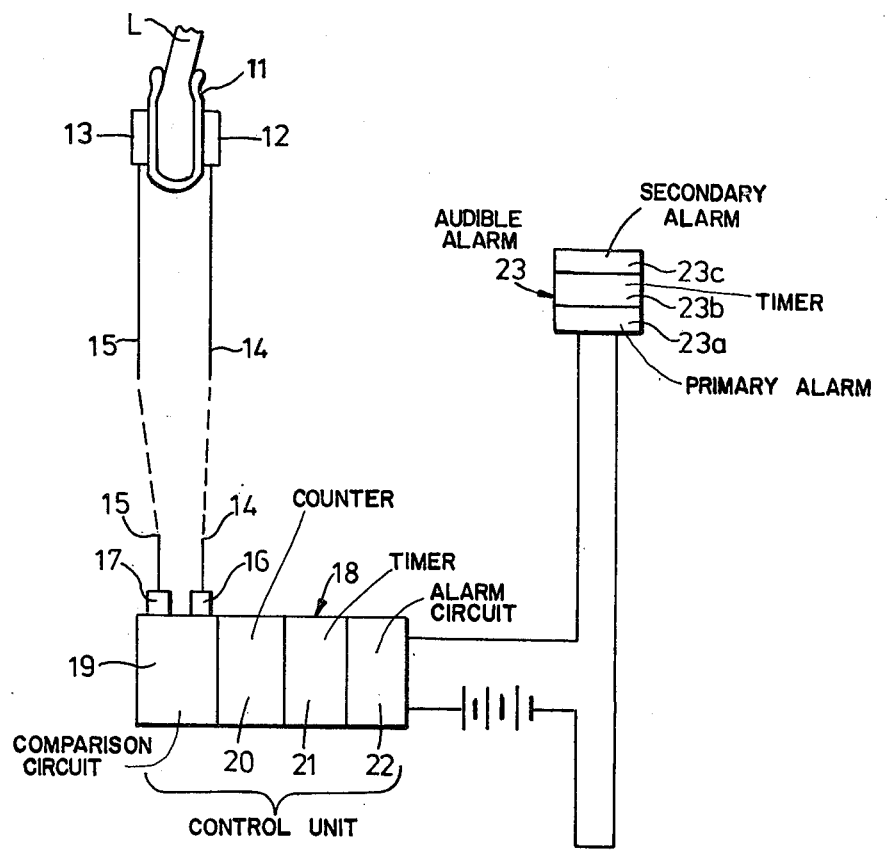

RESPIRATORY MEASURING DEVICES

This invention relates to a respiration measuring device and more particularly to a respiration measuring device for attachment to a patient and including an alarm arranged to actuate when the respiration rate of the patient exceeds a predetermined value.

Respiration detecting and measuring devices are well known in the art and conventionally comprise strain gauges strapped, taped or otherwise secured to the patient's body, generally the chest. Such devices are expensive, require skilled application, maintainance, monitoring and, because of the location and application, awkward and uncomfortable for the patient. Because of these disadvantages the known respiration detecting and measuring devices are rarely found outside hospitals, nursing homes and the like nursing establishments and the devices are used almost exclusively for patients in intensive care or suffering from respiratory problems.

PRIOR ART

In the British Patent Specification No. 1215904 there is disclosed a respiration measuring device in which a temperature sensing element is located in a chamber connected to the nostril of a patient, the element is thus sensitive to changes in air flow temperature at inhaling and exhaling and such changes are displayed by a voltmeter.

Thus, the arrangements for British Patent Specification No. 1215904 displays temperature change but does not disclose any means for counting the temperature changes displayed or utilizing the rate of temperature change.

The present invention seeks to provide a respiration measuring device which is simple in construction, can be applied to a patient with minimal training, and which is far less uncomfortable for the patient than the known respiration detecting and measuring devices.

According to the present invention there is provided a respiration measuring device comprising a temperature sensitive element intended to locate in a breathing duct, or the air flows to and from a breathing duct, a control means for counting temperature changes sensed by said temperature sensitive element, and an alarm adapted to be activated by said control means when the rate of temperature changes sensed by said temperature sensitive element rises above or falls below a predetermined value.

Preferably said temperature sensitive element comprises a thermistor and conveniently the device includes an amplifier for amplifying the output of said temperature sensitive element.

In a preferred form said control means comprise an electronic counter and timer arrangement.

Preferably the device includes a second temperature element located adjacent but spaced from the breathing duct and air flows to and from the breathing duct and intended to record ambient temperature. With such an arrangement the output from said second temperature sensitive element is conveniently received by said control means and said control means preferably compares the signals received from the first temperature control means with the signals received from said second temperature sensitive element.

When the device includes a second temperature sensitive element the device preferably includes an amplifier for amplifying the output from said second temperature sensitive element.

In a preferred embodiment in accordance with the invention said first and second temperature sensitive elements are arranged on a clip adapted to attach to a patient's nostril so as to present the first temperature sensitive element in the nostril and the second temperature sensitive element out of the nostril and out of the air flows to and from the nostril.

In one embodiment said alarm comprises an audible and/or visual alarm.

As stated hereinbefore the conventional respiratory devices are used by nursing staff to monitor the condition of patients but the device of the present invention, by its simplicity of application, allows the device to be self administered and the provision of an "automatic" alarm allows the device to be used without supervision by a second party. Thus, the device can be self administered by normally healthy persons and used for purposes for which the conventional respiration measuring devices are not suited.

When a person is asleep there are certain periods when the sleeper may experience dreams, two types of which may be defined as "unpleasant" dreams in which the sleeper experiences unpleasant dreams over which he or she has no control, and other so called "lucid" dreams when the sleeper may experience a dream, be aware that he/she is dreaming, and thereby control the contents and course of the dream.

It is well known that an unpleasant dream can be interrupted by a second party waking the sleeper, but the applicant noted that the unpleasant dream can be terminated by a sensory alarm which does not wake the sleeper to full awareness but prompts the sleeper into such awareness within the dream that thereafter the sleeper can control the dream and passes from an unpleasant dream state to a lucid dream state.

It has been found in practice that an "alarm" suitable for interrupting an unpleasant dream without waking the sleeper may comprise a gentle sensory stimulant, such as a light or music or electric shock treatment.

It has also been observed that the respiration rate of a sleeper varies in accordance with the dream states experienced and thus, for example, an adult may exhibit a respiration rate in the region of 9 cycles/min. for slow wave sleep, 12 cycles/min. for most dream sleep states and 15 or more cycles/min. for unpleasant dreams.

Thus, the respiration measuring device proposed by the present invention is particularly suited for use in prompting a sleeping person from an unpleasant sleep state and, when used for this purpose, the alarm preferably comprises an electric shock, conveniently applied to the sleeper via electrodes strapped or otherwise secured to the sleeper, and preferably the shocks are applied to the sleeper in accordance with a pattern which can be recognised by the sleeper.

Preferably the respiration measuring device includes a primary alarm, intended to prompt the sleeper from an unpleasant sleep state, and a secondary alarm intended to wake the sleeper if the primary alarm has actuated for a predetermined time period without change in the respiration rate of the sleeper.

By this arrangement, the primary alarm will be activated when the respiration rate of the sleeper exceeds the predetermined value and, if effective, the respiration rate will fall and the primary alarm will be de-activated. If however, the primary alarm is activated and does not prove effective in reducing the respiration rate within a predetermined time period the secondary alarm is activated to wake the sleeper and thus, effectively terminate the unpleasant sleep state.

When used simply as a means for arresting unpleasant dreams the "predetermined value" of respiration will be between the lucid sleep state respiration rate for the sleeper and the unplesant sleep state respiration rate.

In the normal dream state (respiration rate in the region of 12 cycles/min.) the sleeper may experience normal dreams or lucid dreams and, by setting the predetermined value of respiration rate to a lower level so that said value lies within, or just below, the "normal" respiration rate (12 cycles/min.) the percentage of dreams over which the sleeper has control may thereby be increased.

The invention will now be described further by way of example with reference to the accompanying drawings in which the single FIGURE shows, diagrammatically, a respiration measuring device in accordance with the invention.

In the illustrated example a lightweight U-shaped clip 11, conveniently of a plastics material, embraces the lateral cartilage L of a sleeper's nose to support a first thermistor 12 within the nostril of the sleeper and a second thermistor 13 externally of the sleeper's nose and clear of the air flows from the nostrils.

The outputs of thermistors 12 and 13 are extended via conductors 14 and 15 respectively to amplifiers 16 and 17 respectively and the outputs from amplifiers 16 and 17 are applied to a control unit 18.

The control unit 18 includes a comparison circuit part, designated 19, in which the signals from amplifiers 16 and 17 are compared, a counting part 20 adapted to count each difference in the signals detected by part 19, and a timer part 21 intended to actuate an alarm circuit part 22 as and whilst the counted signals over a given time period rises above a predetermined rate.

The control unit 18 may be powered by a connection with the mains (not shown) or by a battery (not shown) and the alarm circuit part 22 includes a switch or relay which, when actuated to an alarm condition, completes the circuit to an audible alarm, in this case a tape or record player 23. The player will be prepared to play soft and pleasant music at such volume, determined by the distance of the player 23 from the sleeper, as to gently arouse the sleeper from an unpleasant state dream.

Thus, in operation and with the patient asleep, the thermistor 12 records the temperature of air flowing into the nostrils and the warmer air exhaling so that the output of thermistor 12 varies per breathing cycle of the sleeper. The output from thermistor 12 amplified by amplifier 16 and extended to comparison part 19 of unit 18 is compared with the amplifier signal from thermistor 13, detecting ambient temperature, so that the device is automatically balanced against the changes in ambient temperature which occur during the sleep period.

With the sleeper in normal slow wave sleep the respiration rate will be normal, the alarm circuit part 22 will remain unoperated and the circuit for player 23 will therefore be open and inoperative.

If now the sleeper enters an unpleasant dream sleep state an increase in respiration rate will result, the comparison circuit part 19 will detect the increased rate of respiration, the output of part 19 to parts 20 and 21 will exceed the "predetermined" rate of respiration to which the counter and timer 21 are set, and the alarm circuit part 22 will therefore be actuated to close the circuit to player 23. When player 23 is actuated the output from the player 23 will disturb the sleeper from the unpleasant dream state, the respiration rate will fall and, as said rate falls below the predetermined rate, the alarm circuit part 22 will become inactive, the circuit to the player 23 will open and the player will become inactive. Thus, by carefully controlling the volume and type of sounds from the player 23 an unpleasant dream state may be terminated without awaking the sleeper.

In an alternative arrangement alarm 23 may be an electric shock treatment apparatus arranged to give the sleeper electric impulse stimulation to a pattern recognizable by the sleeper. Such recognition being achieved by for example, applying the alarm while the patient is awake.

Further, the alarm arrangement 23 may include a primary alarm 23a intended to apply a mild stimulation intended to bring the sleeper from an unpleasant sleep state to a controlable dream state, a timer 23b activated with the primary alarm 23a, and a secondary alarm 23c, intended to be activated when the timer has been operated for a predetermined period of time, and which, when actuated, positively wakes the sleeper.

Although described with reference to use in awakening a sleeper from an unpleasant dream state the respiration measuring device proposed by the invention is not limited thereto and the device may be used in the conventional role to monitor the respiration rate of patients. In such a role the counter 20 and the timer 21 may be arranged to actuate alarm circuit part 22, if the respiration rate of the patient exceeds a predetermined value or falls below a predetermined value, and the alarm activated by the alarm circuit part 22 will be suitably arranged to draw the attention of the nursing staff to the patient experiencing respiratory difficulties.

Thus many modifications and variations in the form and application of the device the subject of the specific embodiment will be apparent to persons skilled in the art.

I claim:

1. A respiration rate measuring device for measuring the respiration rate of a person comprising, in combination,
   (a) a temperature sensitive element intended to locate in a breathing duct or the air flow to and from a breathing duct of the person,
   (b) means for locating said element in said breathing duct or in said air flow,
   (c) control means for counting temperature changes sensed by said temperature sensitive element, and
   (d) alarm means actuated by said control means when the rate of temperature change sensed by said temperature sensitive element rises above a predetermined value characterized in that
   (e) said alarm means includes means effective on the person to whom the device is fitted, to make the person, when asleep, aware that the alarm means has actuated without being shocked from sleep.

2. A respiration measuring device as claimed in claim 1 and wherein said temperature sensitive element comprises a thermistor and said device further includes an amplifier connected to said thermistor for amplifying the output of said thermistor, said amplifier having an output connected to said control means.

3. A respiration measuring device as claimed in claim 1 including a second temperature sensitive element adapted to be located in a position adjacent but spaced from the breathing duct and air flow to and from the breathing duct for recording ambient temperature, means for locating said second element in said position, and wherein said control means includes means to compare the signals received from the first temperature sensitive element with the signals received from said second/sensitive element to detect the respiration rate.

4. A respiration measuring device as claimed in claim 1 in which said alarm means comprises an audible alarm.

5. A respiration measuring device as claimed in claim 1 in which said alarm means comprises a visual alarm.

6. A respiration measuring device as claimed in claim 1 in which the alarm means includes means to apply sensory stimulation to the patient in the form of electric shock patterns.

7. A respiration measuring device as claimed in claim 1 in which said alarm means includes a primary alarm, a timer connected for actuation with the primary alarm, and a second alarm connected to and adapted to be actuated by the timer after the primary alarm has been actuated for a predetermined period of time.

* * * * *